UNITED STATES PATENT OFFICE.

J. W. MOFFITT, OF HARRISBURG, PENNSYLVANIA.

IMPROVEMENT IN MANUFACTURE OF PORCELAIN TEETH.

Specification forming part of Letters Patent No. 30,684, dated November 20, 1860; Reissue No. 1,122, dated January 8, 1861.

*To all whom it may concern:*

Be it known that I, J. W. MOFFITT, of Harrisburg, in the county of Dauphin and State of Pennsylvania, have invented a new and useful Improvement in the Manufacture of Artificial Teeth and Gums; and I do hereby declare that the following is a full and exact description of the same.

The nature of my invention consists in the manufacture of teeth and gums (upon a platina plate, which has been previously "fitted" to the mouth of the subject) of the materials hereinafter specified, in the proportions described, the said materials being prepared, applied, and consolidated upon the said plate substantially in the manner hereinafter described, whereby I am enabled to produce artificial teeth and gums of porcelain in the condition which I call "non-sectional block-work," or a sufficient portion of the same for either jaw, in one homogeneous, solid, and continuous "block," with scarcely any appreciable variation in the length or form of the curve of the same from the action of heat in their manufacture, that will not be subject to subsequent cracking, shelling, or breaking from sudden exposure to changes of temperature, as in cleaning or use.

To enable others to understand and practice my invention, I will proceed to give, first, a list of the materials used; secondly, the proportions thereof required to constitute the several primary compounds; and, thirdly, the manner of applying and combining them together or upon the plate.

First. The materials used are Delaware spar, silex, kaolin clay, white flint-glass, French china, glass of borax, salts of tartar, titanium, and platina sponge. In selecting and preparing these materials I proceed as follows: I select the spar so as to have it free from iron or other impurities, heat it in the muffle of a furnace to a bright red, then plunge it into cold water, and afterward grind it fine in a mortar. The silex selected should be of the crystallized character, and is treated in the same manner as described for the spar. The flint-glass should be selected from the hardest kind. The French china is obtained from the French chinaware. The clay, salts of tartar, titanium, and platina sponge should also be pure.

Secondly. Of these materials I take, for what I call "No. 1 body of the teeth," of Delaware spar, thirteen ounces; silex, three ounces; kaolin clay, ten grains; white flint-glass, one pennyweight and six grains; French china, one pennyweight and six grains; flux, fifteen grains, and of titanium, say, from twenty to sixty grains, as the required color of the body may render proper. Each of these materials must be carefully ground to a fine powder, accurately weighed by Troy weight, and intimately mixed together in a mortar, the titanium being first put in, and the other materials added gradually and intimately mixed therewith. For what I call "No. 2 body of the teeth" I take of "body No. 1," one ounce, (Troy;) flint-glass, from sixteen to twenty grains, (Troy;) and after grinding the glass very fine I mix it intimately in a mortar with the other matter, and grind them together into an impalpable powder. For No. 1 blue enamel I take, of Delaware spar, four ounces; flux, twenty-four grains; flint glass, twenty-four grains; platina sponge, say, from twelve to sixty grains, as the color desired may require, and mix them intimately together. For No. 2 blue enamel I take of blue enamel No. 1, one ounce; flux, three grains; flint-glass, three grains, and mix them intimately together. For yellow enamel I take of blue enamel No. 1, two ounces; titanium, say, from fourteen to twenty grains, and mix them intimately together. Each of the said enamel compounds must have their constituents accurately weighed (by Troy weight) and ground to an impalpable powder. For the "flux" I take of glass of borax, four pennyweights; salts of tartar, three pennyweights; Delaware spar, two ounces, and grind each very fine in a mortar, and then intimately mix them together. The compound is then packed into a suitable crucible previously lined with a batter of kaolin clay, and then closed, (by luting into its mouth by some of the same batter a piece of fire-clay slab,) dried, and finally put into a strong fire for fifteen or twenty minutes. The compound, having been thus fused, is then cooled, the crucible broken from it, and, if the mass be found clear and free from stains, it is then to be ground very fine and kept for use as flux.

Thirdly. I will now proceed to describe the manner in which I apply and consolidate portions of these different "primary compounds" together upon "the plate," so as to produce the improved manufacture specified. A platina plate having been prepared and adapted to fit the mouth of the subject, as heretofore, and also fitted with platina supporting-pins in any suitable manner, and a matrice having also been provided (as for carving ordinary block-work) and applied to the plate, I take a sufficient quantity of the material called "No 1 for the body of the teeth," and mix it with water to a thick paste, and, after oiling the matrice, pack it into the latter, tapping the matrice with my finger to drive out any confined air, in the usual manner, after which I generally cut away the mass at the cutting-edge part of the teeth to half their intended final thickness, and as far up toward the gum part as the teeth are intended to reach. The space thus left by the cutting is then filled in with some of the same "body" ground to impalpable fineness. The whole piece, however, may be formed entirely of this more finely-ground body, if preferred, as it is not necessary to the final result required that the coarser body be used for the base. The piece is now ready for carving, which is done in the usual manner, after the completion of which I apply the "enamels," the same being mixed with water to the consistency of cream in the usual manner. The yellow enamel I apply first at the neck parts of the teeth. Then the No. 1 blue enamel is applied, so as to overlap the yellow, and also reach down over the cutting-edges of the teeth. The carving and enameling having been thus completed, the piece is ready for the baking process, which is accomplished by placing it upon a "slide," the plate being embedded in kaolin clay or its equivalent, and introducing it slowly into the muffle of a heated furnace in the usual well-known manner. After it has come to the point of fusion, which requires from fifteen to twenty minutes, it should be withdrawn and allowed to cool in the air; and if there should then be found any imperfections or defects in the same, they must be remedied by applying No. 2 body to those which may be found in the body, and No. 2 blue enamel to those which may be found in the teeth, and then baking in the furnace, as before. After the piece has again cooled in the air, any of the usual well-known gum-enamels of an easy flowing or fusing nature is applied to the gum in the usual manner, and the piece again placed upon the slide with the teeth upward, being careful to have the piece horizontal in position, and to introduce it very slowly into the muffle of the furnace, so as to allow the heat to come upon it gradually and until the said gum-enamel flows. It is then finally cooled down in a warm muffle, and the plate afterward "finished" in the ordinary manner, ready for insertion into the mouth of the subject, it having undergone scarcely any appreciable permanent change in either the length or form of the curve, and will be entirely free from all liability to the subsequent cracking, shelling, or breaking from exposure to sudden changes of temperature heretofore incident to porcelain teeth and gums made in a continuous block, because the materials, in the proportions specified, when the same are applied and consolidated upon the plate substantially in the manner described, are such as to cause the said teeth and gums to expand and contract in perfect harmony with the expansion and contraction of the plate, and therefore not only to preserve the original general form of the piece in baking it, but to render it free from all subsequent liability to strain from sudden changes of temperature in the mouth containing it, or when suddenly exposed to cold air, or when placed, while warm, in cold water.

I am aware that most of the materials and manipulations herein specified have been used or practiced before, and that continuous porcelain teeth and gums have before been made upon a platina plate; but the want of uniformity heretofore in the expansibility and contractibility of the plate and the consolidated materials thereon, when the piece is exposed to sudden changes of temperature, causes a strain which renders the teeth and gums subject to cracking or breaking throughout their substance, and also to the separating of the gum from the plate in using. Therefore I do not wish to claim, broadly, the manufacture of porcelain teeth and gums in a continuous or solid block upon a plate; but Having fully specified all the materials which I use, described the whole process of manufacture, and pointed out the utility of the same, what I claim as new therein of my invention, and desire to secure by Letters Patent, is—

The manufacture of porcelain teeth and gums of the material specified, in the proportions described and set forth, the same being prepared, applied, and consolidated together upon the plate substantially in the manner described, and for the purpose specified.

J. W. MOFFITT.

Witnesses:

BENJ. MORRISON,

JAMES MCCAHEN.